US006733775B1

(12) United States Patent
Klein et al.

(10) Patent No.: US 6,733,775 B1
(45) Date of Patent: May 11, 2004

(54) PLASTIC FILMS, ESPECIALLY FOR USE IN A DERMAL OR TRANSDERMAL THERAPEUTIC SYSTEM

(75) Inventors: Robert-Peter Klein, Neuwied (DE); Reinhold Meconi, Neuwied (DE); Ursula Götte, Unkel (DE)

(73) Assignee: LTS Lohmann Theraphie Systeme, AG, Andernach (DE)

( * ) Notice: Subject to any disclaimer, the term of this patent is extended or adjusted under 35 U.S.C. 154(b) by 0 days.

(21) Appl. No.: 10/070,657

(22) PCT Filed: Aug. 26, 2000

(86) PCT No.: PCT/EP00/08332

§ 371 (c)(1),
(2), (4) Date: Jun. 10, 2002

(87) PCT Pub. No.: WO01/19351

PCT Pub. Date: Mar. 22, 2001

(30) Foreign Application Priority Data

Sep. 10, 1999 (DE) .......................... 199 43 317

(51) Int. Cl.⁷ .................. A61F 13/00; A61K 9/70
(52) U.S. Cl. ............. 424/449; 424/400; 424/443; 424/447; 425/461
(58) Field of Search .......................... 424/400, 443, 424/447, 449; 425/461

(56) References Cited

U.S. PATENT DOCUMENTS 5,593,684 A    1/1997    Baker et al. ............. 424/435
5,662,925 A  * 9/1997    Ebert et al. ............. 424/447

FOREIGN PATENT DOCUMENTS

| DE | 33 15 272 A | 10/1984 |
| DE | 197 05 138 A1 | 8/1998 |
| EP | 0 186 019 A | 7/1986 |
| EP | 0 384 267 A | 8/1990 |
| GB | 13 19 652 | 6/1973 |
| JP | 5310560 A | 11/1993 |
| JP | 8-116963 | 5/1996 |
| JP | 11-157008 | 6/1999 |
| WO | 96 40355 A | 12/1996 |
| WO | WO 98/34600 | * 8/1998 |

* cited by examiner

Primary Examiner—Thurman K. Page
Assistant Examiner—Konata M. George
(74) Attorney, Agent, or Firm—Birch, Stewart, Kolasch & Birch, LLP

(57) ABSTRACT

A dermal or transdermal therapeutic system comprising a sheet-like substrate or reservoir containing readily volatile auxiliary agents or active agents, which substrate or reservoir is covered on one of its sides with a backing layer impermeable to the ingredients and on the opposite side with a detachable, likewise impermeable protective layer to prevent loss of ingredients during prolonged storage, is characterized in that both the backing layer and the protective layer are made of plastic film which is on both sides with vapour-deposited metal

12 Claims, No Drawings

PLASTIC FILMS, ESPECIALLY FOR USE IN A DERMAL OR TRANSDERMAL THERAPEUTIC SYSTEM

This is application is the national phase under 35 U.S.C. § 371 of PCT International Application No. PCT/EP00/08332 which has an International filing date of Aug. 26, 2000, which designated the United States of America.

This invention relates to plastic films, which are coated on both sides with vapour-deposited metal and are meant to be used, in particular, for reducing the uptake of active substances in a dermal or transdermal therapeutic system, comprising a sheet-like substrate or reservoir containing readily volatile auxiliary agents and/or active agents, which substrate or reservoir is covered on one of its surfaces with a backing layer impermeable to the ingredients and on the opposite side with a detachable protective layer to prevent loss of ingredients during prolonged storage.

Transdermal therapeutic systems (TTSs) commonly comprise a backing layer impermeable to active or auxiliary agents, an active agent-containing layer and a detachable protective layer. The material from which the impermeable backing layer and the removable protective layer are made is commonly selected so as to absorb as little active substance as possible.

In the case of readily evaporating active agents such as nitroglycerine and nicotine, however, the selection of the materials turns out to be difficult. According to the state of the art, plastic films are used which are unilaterally metallized on the side which comes into contact with the active agent-containing layer. This measure, however, fails to satisfactorily prevent active substance loss, which loss occurs as a result of active substance escaping from the cutting edges of the transdermal therapeutic system, precipitating on the exposed side of the impermeable backing layer and the detachable protective layer, and being absorbed by the material of these layers.

EP 0 186 019 describes, in Example 1, a transdermal therapeutic system, which contains in its active substance-containing layer nitroglycerine adsorbed to lactose. During storage, however, the active ingredient-containing layer experiences a loss in nitroglycerine, namely approximately 16% over a period of 12 months. This means that the known transdermal therapeutic system is unstable and does not comply with pharmaceutical requirements.

DE 33 15 272 describes a transdermal therapeutic system having a layered active substance reservoir structure. According to Example 1, nitroglycerine adsorbed to lactose is used as active agent. As cover layer and/or for the removable protective layer, films are used that are made of various polymeric substances, such as polyethylene terephthalate, which may he aluminized on one side. However, the results obtained from stability tests show that in the course of 15 months the reservoir layer loses about 11% of nitroglycerine, about 6% of which are present in the cover layer and about 5% in the removable protective layer. From the pharmaceutical point of view, a loss of active substance of approximately 11% in 15 months is unacceptable.

The object of the present invention is to provide a dermal or transdermal therapeutic system containing readily volatile active agents or auxiliary agents which is formed such that, obviating the difficulties and technical restrictions existing in the state of the art and leading to loss of active and auxiliary agents, such loss is almost entirely prevented, even in the case of prolonged storage.

It has turned out, surprisingly, that this object is achieved by double-face vapour deposition of metal on plastic films according to the main claim.

The amount of metal vapour-deposited on the plastic films may be 10–500 mg/$M^2$, but preferably 40–200 mg/$M^2$, per side, the plastic films preferably being aluminized.

The plastic films provided on both sides with vapour-deposited metal may be rendered adhesive on one or on both sides. This is necessary above all if the plastic film provided with double-side metallization is used as a detachable protective layer. To render the double-side-metallized plastic films adhesive, one commonly employs silicone polymers.

The plastic films may be selected from the group of polyester, polyethylene, polypropylene, polyamide, polyurethane, polyvinyl chloride, polyvinylidene chloride, polyvinyl alcohol and ethylene-vinyl acetate copolymer.

For vapour deposition of metals, the plastic films may be employed on their own, but they can also be combined with each other. Thus, the plastic film may also be a laminate of two or more, different, layers of plastic.

Commonly, the plastic films have a thickness from 0.004–1.0 mm, preferably 0.010–0.5 mm.

The plastic films provided on both sides with vapour-deposited metal, which may in addition be rendered adhesive, are preferably used in the manufacture of sheet-like medicaments comprising readily volatile ingredients.

The double-face vapour deposition of metals on the plastic films takes place under high-vacuum or with the aid of a plasma, and can be carried out in one or more operations.

EXAMPLE 1

In a thin-layer-chromatography glass chamber was placed enough nitroglycerine lactose trituration (10% nitroglycerine) for the bottom to be well covered. In the vapour chamber were hung film samples (16 $cm^2$), and placed in a drying cabinet heated to 40° C. At time intervals of 1.2 or 3 months, respectively, samples were taken. These samples were rinsed with methanol to remove the adsorbed active agent. Then the test samples were exhaustively extracted with methanol, and the active substance was determined.

TABLE 1

| Type of Film: | Nitroglycerine Content ($\mu g/cm^2$) Storage Time (months) | | |
|---|---|---|---|
| 100 $\mu$m PET | 1 | 2 | 3 |
| siliconized on both sides | 0,96 | 0,88 | 1,28 |
| aluminized on one side and siliconized on both sides | 0,71 | 0,55 | 0,85 |
| aluminized on both sides and siliconized on both sides | 0,05 | 0,12 | 0,11 |

As shown by the results (Tab. 1), a PET film (100 $\mu$m) which is aluminized on both sides and siliconized on both sides absorbs only about 1/10 of the amount of nitroglycerine absorbed by a non-aluminized film (with 3 months' storage at 40° C.).

EXAMPLE 2

The test conditions were analogous to those in Example 1; as active substance nicotine was used.

TABLE 2

| Type of Film: | Nicotine ($\mu g/cm^2$) Storage Time (months) | | |
|---|---|---|---|
| 100 $\mu$m PET | 1 | 2 | 3 |
| siliconized on both sides | 0,24 | 0,59 | 0,75 |
| aluminized on one side and siliconized on both sides | 0,22 | 0,41 | 0,68 |
| aluminized on both sides and siliconized on both sides | 0,05 | 0 | 0,17 |

As verified by the results, here too, double-face aluminizing has clearly reduced the active substance absorption of 100 $\mu$m pet film.

What is claimed is:

1. Dermal or transdermal therapeutic system comprising a sheet-like substrate or reservoir containing readily volatile auxiliary agents or active agents, which substrate or reservoir is covered on one of its sides with a backing layer impermeable to the ingredients and on the opposite side with a detachable, likewise impermeable protective layer to prevent loss of ingredients during prolonged storage, wherein
both the backing layer and the protective layer are made of plastic film which is impermeably coated on both sides with vapour-deposited metal.

2. The therapeutic system according to claim 1, wherein the amount of metal which is vapour-deposited per unit area is 10 to 500 mg/m².

3. The therapeutic system according to claim 1, wherein the vapour-deposited metal is aluminium.

4. The therapeutic system according to claim 1, wherein the plastic films of the protective layer, which are provided with a vapour-deposited metal layer, are rendered adhesive on at least one side.

5. The therapeutic system according to claim 1, wherein the plastic films are selected from the group of polyester, polyethylene, polypropylene, polyamide, polyurethane, polyvinyl chloride, polyvinylidene chloride, polyvinyl alcohol and ethylene-vinyl acetate copolymer.

6. The therapeutic system according to claim 1, wherein the plastic films have a thickness between 0.004 to 1.0 mm.

7. The therapeutic system according to claim 1, wherein it the sheet-like substrate or reservoir contains nitroglycerine as an ingredient.

8. The therapeutic system according to claim 1, wherein the sheet-like substrate or reservoir contains nicotine as an ingredient.

9. A process for the manufacture of plastic films, provided with a vapour-deposited metal layer, for the transdermal therapeutic system according to claim 1, wherein to obtain absolutely impermeable double-face metal layers, the vapour deposition is performed under high vacuum in at least one operation.

10. A process for the manufacture of plastic films, provided with a vapour-deposited metal layer, for the transdermal therapeutic system according to claim 1, wherein to obtain absolutely impermeable metal layers, the vapour deposition is performed with the aid of a plasma in at least one operation.

11. The therapeutic system according to claim 2, wherein the amount of metal which is vapour-deposited per unit area is 40 to 200 mg/m².

12. The therapeutic system according to claim 6, wherein the plastic films have a thickness preferably between 0.010 to 0.5 mm.

* * * * *